United States Patent
Steinwandel et al.

(10) Patent No.: US 9,097,745 B2
(45) Date of Patent: Aug. 4, 2015

(54) CORROSION DETECTION APPARATUS FOR MONITORING A STATE OF CORROSION

(75) Inventors: Juergen Steinwandel, Uhldingen-Muehlhofen (DE); Ulrike Heckenberger, Munich (DE); Theo Hack, Hoehenkirchen-Siegertsbrunn (DE)

(73) Assignee: EADS Deutschland GmbH, Ottobrunn (DE)

( * ) Notice: Subject to any disclaimer, the term of this patent is extended or adjusted under 35 U.S.C. 154(b) by 390 days.

(21) Appl. No.: 13/640,931

(22) PCT Filed: Apr. 8, 2011

(86) PCT No.: PCT/EP2011/055538
§ 371 (c)(1),
(2), (4) Date: Nov. 29, 2012

(87) PCT Pub. No.: WO2011/128271
PCT Pub. Date: Oct. 20, 2011

(65) Prior Publication Data
US 2013/0069676 A1 Mar. 21, 2013

(30) Foreign Application Priority Data
Apr. 14, 2010 (DE) .......................... 10 2010 014 918

(51) Int. Cl.
*G01R 27/08* (2006.01)
*G01R 27/02* (2006.01)
*G01N 17/04* (2006.01)

(52) U.S. Cl.
CPC .............. *G01R 27/02* (2013.01); *G01N 17/043* (2013.01)

(58) Field of Classification Search
CPC ............................... G01R 27/02; G01N 17/043

USPC .................. 324/700, 699, 693, 691, 649, 600
See application file for complete search history.

(56) References Cited

U.S. PATENT DOCUMENTS 5,243,298 A   9/1993 Runner
5,286,357 A   2/1994 Smart et al.
(Continued)

FOREIGN PATENT DOCUMENTS

DE   10 2006 030 519 A1   12/2007
JP         01197629 A  *  8/1989  .............  G01N 17/00
(Continued)

OTHER PUBLICATIONS

Simonen et al., "Wireless Sensors for Monitoring Corrosion in Reinforced Concrete Members", Proceedings of the SPIE—The International Society for Optical Engineering SPIE, 2004, vol. 5391, No. 1, pp. 587-596, XP-002640210 (ten (10) sheets).
(Continued)

*Primary Examiner* — Hoai-An D Nguyen
(74) *Attorney, Agent, or Firm* — Crowell & Moring LLP

(57) ABSTRACT

A corrosion detection apparatus for permanently and integrally monitoring a state of corrosion of a component is provided. The corrosion detection apparatus makes it possible to use the change in electrical conductivity to detect corrosion of a component to be monitored. A corrosion-sensitive bridging element that establishes an electrical connection between a first electrical line section and a second electrical line section of a sensor circuit is used to change certain electrical properties of the sensor circuit. On account of the corrosion-sensitive property of the bridging element, the latter changes its electrical conductivity when corrosion starts. This makes it possible to use the sensor circuit to detect corrosion of the bridging element and thus of the component to be monitored.

14 Claims, 3 Drawing Sheets

(56) References Cited

U.S. PATENT DOCUMENTS

| | | |
|---|---|---|
| 6,282,947 B1 * | 9/2001 | Schon et al. .............. 73/53.01 |
| 2006/0125493 A1 | 6/2006 | Subramanian et al. |
| 2007/0163892 A1 | 7/2007 | Haridas |
| 2008/0204275 A1 | 8/2008 | Wavering et al. |
| 2009/0058427 A1 | 3/2009 | Materer et al. |
| 2009/0162076 A1 | 6/2009 | Wang et al. |

FOREIGN PATENT DOCUMENTS

| | | |
|---|---|---|
| JP | 7-113740 A | 5/1995 |
| WO | WO 2009/016594 A2 | 2/2009 |
| WO | WO 2009/103302 A1 | 8/2009 |

OTHER PUBLICATIONS

International Search Report with English translation dated Jun. 17, 2011 (six (6) sheets).

German-language Written Opinion (PCT/ISA/237) (five (5) sheets).

German Office Action dated Sep. 21, 2010 (eleven (11) sheets).

* cited by examiner

CORROSION DETECTION APPARATUS FOR MONITORING A STATE OF CORROSION

REFERENCE TO RELATED APPLICATIONS

The present application claims the priority of the German patent application No. 10 2010 014 918.7 filed on Apr. 14, 2010, the entire disclosure of which is incorporated herein by reference.

FIELD OF THE INVENTION

The invention relates to a system for documenting corrosion on components or in corrosive ambient conditions. In particular, the invention relates to a corrosion detection apparatus for permanently and integrally monitoring a state of corrosion of a component as well as of an aircraft using such a corrosion detection apparatus.

TECHNICAL BACKGROUND

Due to extended vehicle operating times, which can be, for example, up to 30 years in the case of aircraft, the protection of metal structural components against occasional corrosion is of special importance. A majority of the materials that are used in the aviation industry involve aluminum alloys. Locations that evade direct visual inspection altogether or that are only accessible with considerable effort and known to be potentially exposed to more extensive exposure to water and electrolytes, should be monitored for corrosion at regular intervals.

Civil aircraft and military transporters operate more or less regularly inside climate zones of high air humidity and high ambient temperatures such as, for example, in maritime atmospheres, which are conducive to the formation of condensation.

The prior art specifies moisture sensors that are provided with a water-sensitive layer for detecting instantaneous moisture. These sensors are typically configured as thin-layer systems and operate reversibly, depending on the respectively occurring outer instantaneous partial pressure of $H_2O$. Any reversible take-up of water in the sensitive layer on or into the condenser causes a change of the capacitance, whereby this change constitutes the measured value in these sensors. However, sensors of this type are not able to detect an integral take-up of $H_2O$ or electrolytes directly.

SUMMARY OF THE INVENTION

Exemplary embodiments of the present invention provide better corrosion detection.

Disclosed herein are a corrosion detection apparatus for permanently and integrally monitoring a state of corrosion of a component or for detecting corrosive ambient conditions, as well as an aircraft having a corrosion detection apparatus.

The detailed embodiments refer both to the corrosion detection apparatus and the aircraft. In other words, characteristics that are described below in relation to the corrosion detection apparatus can be implemented in the aircraft in an identical manner, and vice versa.

According to one embodiment of the invention, a corrosion detection apparatus for permanently and integrally monitoring a state of corrosion of a component or of a corrosive ambient environment is provided. The corrosion detection apparatus includes a sensor circuit for detecting corrosion on the component, wherein the sensor circuit includes a first electrical line section and a second electrical line section. Furthermore, the sensor circuit includes a bridging element that is sensitive to corrosion having a first end and a second end, wherein, in an initial state the first end is in electrical connection with the first line section and the second end is in electrical connection with the second line section. In the initial state the corrosion-sensitive bridging element has a first electrical conductivity and in a corrosion state it has a second electrical conductivity, such that the sensor circuit is able to detect corrosion on the basis of a change-over from the first to the second conductivity.

The aspect of "permanent and integral monitoring" must be understood in contrast to instantaneous measurements of moisture. In other words, using the invention, it is possible to take into account and/or measure the entirety of the environment that has been instrumental in causing corrosion since the installation of the corrosion detection apparatus.

This can translate into an improvement of security such as, for example, in air traffic security. Taking reliable measurements of the state of corrosion in places of a component or item that currently is otherwise difficult to access is now possible. Using electrical lines, the measured values can be sent, for example, to central computing centers, where they are more easily accessible to the user.

In addition, in the context of the present embodiment and any further embodiment of the invention, the term "sensitive to corrosion or corrosion-sensitive" is to be understood as follows: the bridging element changes its physical state and with that the electrical conductivity thereof due to corrosion on a scale over time that is shorter than the length of operation of the component that is to be monitored. Consequently, proof of corrosion according to the invention on the component can be detected still during the operative use of the component.

The corrosion-sensitive bridging element can have the same sensitivity regarding corrosion as the component that is to be monitored. This can be achieved, for example, by using the same material from which the two components are made. However, sensitivity deviating from this is also possible.

Based on the corroded state of the bridging element, it is subsequently possible to detect in the manner as described corrosion on the bridging element and thereby on the component.

In other words, the corrosion-sensitive bridging element constitutes an electrical connection that can be reversed, and thereby interrupted, by means of corrosion. This interruption of the connection due to corrosion can subsequently be detected by the sensor circuit.

For example, a previously bridged condenser can now be read in an AC circuit and the capacitance of the same can be determined. This is not possible in the initial state with a non-corroded bridging element. However, bridging a different element of the sensor circuit by means of the bridging element is also possible, such as, for example, a coil or even conducting paths of the sensor circuit, that can be included for providing voltage to the sensor circuit.

In other words, the sensor circuit is configured such that it allows for measuring the electrical properties of a combination taken from the first line section, the second line section, and the corrosion-sensitive bridging element.

Therefore, the sensor circuit is configured in such a way that, upon implementing a measurement of the electrical properties of this combination, the measured value clearly answers the question as to whether corrosion has occurred on the corrosion detection apparatus and, therefore, on the component to be monitored. The electrical property therein can be, for example, the capacitance of a condenser, the attenuation of an resonant circuit, the amplitude of an resonant circuit and/or the frequency of an resonant circuit.

In other words, the corrosion detection device of the present invention provides a sensor that directly allows for integrated water take-up and/or a water effect relative to the component that is to be monitored. The same is also possible with regard to the take-up and/or effect of electrolytes. A cost-effective apparatus that is easy to produce can be provided for taking measurements, in particular, in places that evade any direct visual inspection altogether or that are only accessible with considerable effort, such as, for example, on aircraft, and which are known to be potentially extensively subjected to the effects of water and/or electrolytes.

It is possible, for example, to provide a bridging element in form of a wire or a thin layer; over time and also under the influence of corrosive effects, the same becomes corroded, thus changing the electrical conductivity thereof. This change in electrical conductivity can provide the user with information, as part of a read-out process of the sensor circuit, as to whether there is corrosion present on the bridging element in comparison to a reference state.

It is possible therein for the first electrical conductivity to be greater or smaller than the second electrical conductivity. It is also possible for the corrosion-sensitive bridging element to be selected in terms of the material, thickness, possible additional layers of corrosion-resistant finish thereof such that a complete destruction occurs in one partial region of the bridging element, which is caused by corrosion. The result is that the electrical bridging action between the first electrical line section and the second electrical line section is interrupted. In this case, electrical conductivity can have the value 0.

According to a further embodiment of the invention, the first electrical line section is configured as a first electrode of a condenser, and the second electrical line section is configured as a second electrode of the condenser.

In other words, the sensor circuit contains a condenser having two electrodes that are short-circuited by the corrosion-sensitive bridging element.

In the shorted state, which is also referred to as the initial state, a read-out of the capacitance of this condenser of the sensor circuit is not possible. In the corrosion state, however, when corrosion processes have interrupted the bridging element, it is possible to take a reading of the capacitance of the condenser in an AC circuit.

The corrosion detection apparatus can contain any necessary electrical components of the AC circuit, such as, for example, a voltage source. However, it is also possible for only two electronic connections to be provided by the corrosion detection apparatus to which the AC circuit is connected. For example, it is possible to provide an aircraft with a plurality of such corrosion detection apparatuses placed at the respectively desired locations in order to subsequently take, one device after the other, a read-out from the sensor circuit in order to gather information regarding the respective state of corrosion.

However, it is also possible to integrate a plurality of such corrosion detection apparatuses as part of the network administration of the corresponding aircraft and to take read-outs from the corrosion detection apparatus and/or the respective sensor circuit of said devices centrally or remotely. This allows for ascertaining as to whether a change of the electrical conductivity of the corrosion-sensitive bridging element, and thereby corrosion of the component that is to be monitored, has set in.

It is possible therein to use an interdigital condenser as a condenser within the sensor circuit, which is essentially used purely as a capacitive element. Similarly, a plate capacitor can be used as well. Furthermore, both condenser types can be configured as a component of a RFID resonant circuit for the touch-less measurement of the respective state the sensor circuit.

According to a further embodiment of the invention, the condenser is an interdigital condenser and the corrosion-sensitive bridging element is embodied as a thin layer between two electrodes of the interdigital condenser.

In other words, the sensor circuit contains an interdigital condenser for detecting corrosion on the component having the benefit of minimal production costs. In addition, advantageously, it is possible to produce the corrosion detection apparatus as an embodied example that is quasi two-dimensional. Because it is possible to produce an interdigital condenser as being flat, the corrosion detection apparatus can be provided in a space-saving manner, and the same can be attached, for example, to aircraft surfaces without resulting in any substantial height increase of said surfaces due to the corrosion detection apparatus. A comparatively minimal increase of the air resistance can be noted as a further advantage.

Furthermore, this way, it is possible to produce the corrosion detection apparatus in a chip design containing an interdigital condenser, whereby the same can be achieved by means of a vapor-deposit method or screen printing. The production costs therein are comparatively low and the methods usable on an industrial scale.

In other words, due to the plurality of intertwining fingers of the condenser within one plane, there is provided the possibility of foregoing the third dimension, which is seen, for example, in the plate condenser.

A further advantage associated with the use of an interdigital condenser (IDC) is that due to the application of an IDC on a component that is to be monitored, subsequently, the inhomogeneous electrical field of the IDC penetrates the material that is to be monitored and the state of the same thereby directly contributing to the capacitance of the IDC. The component thus serves as a dielectric of the IDC. Any change of the state of corrosion of the component can thus be detected based on the change of the dielectric, and thereby as a change of the capacity of the IDC.

In other words, using an interdigital condenser it is possible to detect corrosion in the material that is to be monitored, on the one hand, by the interruption of the corrosion-sensitive bridging element; on the other hand, it is possible to utilize a subsequent capacitance measurement to detect degradation of a coating system of an interdigital condenser that is no longer bridged.

According to a further embodiment of the invention, the thin layer is comprised of the same materials as the component that is to be monitored.

In the case of an aircraft, which is made of aluminum alloys for the most part, the corrosion-sensitive bridging element is made of an aluminum alloy, meaning, for example, the thin layer. Using this embodiment, it is possible to provide a representation on a scale of 1:1 that reflects, by means of the measurement by the sensor circuit, a result such as is in fact present with regard to the state of corrosion of the component.

In this embodiment as well as in other embodiments, the component that is to be monitored therein can be an integral component of a primary structure of the aircraft.

It is also to be noted that a cargo compartment as well as the cabin of an aircraft, such as, for example, on an airplane, can be selected as the place of application for such corrosion detection apparatuses.

According to a further embodiment of the invention, the first electrical line section is configured as a first winding section of a coil, while the second electrical line section is configured as a second winding section of the coil. The corrosion-sensitive bridging element is configured as a connecting wire between the first two winding sections of the coil.

In other words, in this embodiment, a coil is bridged by a connecting wire or a conducting path; the consequence is that a resonant circuit that may be connected either becomes enormously mistuned or is enormously attenuated. Similarly, it is possible for an aperiodic borderline case to occur in this context. This depends on the ratio of resistances, currents and capacitances that are used in the context of a possible resonant circuit.

According to a further embodiment, the corrosion detection apparatus further includes a read-out device designed for measuring electrical properties of a combination consisting of the first line section, the second line section, and the corrosion-sensitive bridging element.

Electrical properties therein can be, for example, the capacitance of a condenser, the attenuation of a resonant circuit, the amplitude and/or frequency of a resonant circuit. Other measurable properties are also possible.

Furthermore, it is possible for the corrosion detection apparatus to include a plurality of electrical resistors in a parallel connection, wherein presently, for example, different resistors can be used. The same can then have varying corrosion sensitivities.

The read-out device can be provided, for example, by connections for the capacitance that is connected to an AC circuit. Similarly, it is possible for the AC circuit to be completely present inside the read-out device. Similarly, an external device, such as, for example, an RFID read-out device, can be used as a read-out device within the meaning of this embodiment of the invention.

According to a further embodiment of the invention, the sensor circuit is configured as a s RFID resonant circuit.

According to this embodiment of the invention, it is possible to provide a RFID resonant circuit with or without energy source, meaning an active or a passive RFID resonant circuit. Similarly, a storage device can be present in the RFID resonant circuit that can be written once or multiple times.

For example, within a RFID resonant circuit, the short in the initial state can occur by bridging the first part of the coil and the second part thereof. Due to this bridging action by a wire and/or a conducting path, this RFID resonant circuit can be, for example, strongly attenuated, mistuned or brought into the aperiodic borderline case.

Furthermore, it is possible to incorporate the corrosion-sensitive bridging element into an RFID resonant circuit by means of a conducting path resistance. For example, this can be an individual ohmic resistor. In this instance, the resonant circuit is active and changes its resonance frequency and attenuation with continually increasing resistance consequent to advancing corrosion on the bridging element, the ohmic resistance. With advancing corrosion, the resonant circuit can be ultimately deactivated, which is exhibited by the impossibility of activating and reading the RFID resonant circuit by means of a read-out device.

For example, an electrical short of a condenser within a RFID resonant circuit can bring it into an inactive state, which is why a read-out cannot be taken by its read-out device. If the corrosion-sensitive bridging element, however, is corroded through and a short is, therefore, no longer present, it is possible for resonant circuit to be activated and read by the read-out device. Thus, detection of this read-out event means for the user that, correspondingly, corrosion is present.

According to a further embodiment of the invention, the RFID resonant circuit includes an antenna for sending and receiving electromagnetic signals to the analog circuit with electrical capacitance and electrical inductivity. Furthermore, in the initial state, the corrosion-sensitive bridging element bridges the RFID resonant circuit electrically.

According to a further embodiment of the invention, the sensor circuit is configured such that a read-out is made possible, which is selected from a group consisting of reverse phase reflecting of the field that is created by a read-out device, weaknesses of the field created by the read-out device, read-out by means of load modulation and any combination thereof.

According to a further embodiment of the invention, the sensor circuit includes a plurality of parallel-connected corrosion-sensitive bridging elements with the bridging elements including different corrosion sensitivities, wherein the plurality of parallel-connected corrosion-sensitive bridging elements is dimensioned in relation to one another such that they correspond to a characteristic of a course of corrosion over time, which can be preset.

In other words, assuming average corrosion stress to apply, it is possible for the user to preset a characteristic of the detection curve over time. This can be achieved, for example, by the selection of different corrosion-resistant resistors.

For example, a course of this kind can be selected such that it features a great incline such that a corresponding proof of corrosion is unmistakable. The comments therein describe a course of a curve and are based on such in which the order of magnitude that is used for the detection of corrosion is plotted over time. This order of magnitude could be, for example, the natural frequency of a resonant circuit or the total resistance of this parallel connection.

For example, using the shape or geometry of the resistor, such as, for example, by means of the diameter, it is possible to provide a different sensitivity to corrosion by the corresponding electrical resistors. However, the use of different materials is also possible. It is possible to make only partial use of coatings that are resistant to corrosion.

With this embodiment, it is also possible to provide for the possibility that the used electrical, parallel-connected resistors can change their electrical conductivity due to corrosion at varying speeds. A first state of corrosion therein is characterized, for example, in that, compared to the initial state, a parallel-connected electrical resistor was destroyed due to corrosion. According to the physical rules of the electrical parallel circuit, this would cause the total resistance of this parallel circuit to increase, which could be determined, for example, within a resonant circuit by means of a changed attenuation. In a second possible state of corrosion, when, for example, a second parallel-connected resistance was interrupted due to corrosion, there results a corresponding second increase of the total resistance, which in turn changes the electrical properties of the sensor circuit. The same can be scaled upward with any number of resistors.

In other words, this parallel circuit of the electrical resistors provides an embodiment in which, aside from the first and the second line sections, at least one corrosion-resistant bridging element also helps to determine the electrical properties of the sensor circuit. Correspondingly, for example, any continual increase in corrosion can be detected on the corresponding component that is to be monitored.

In other words, it is possible to use several resistors and parallel circuits having varying material strengths as a corrosion-sensitive bridging element. Corrosion will first deactivate the resistors having a small material strength. Any residual resistor that is either protected against corrosion by, for example, a coating or that is made of a material resistant to corrosion can ultimately preserve the function of the RFID resonant circuit. For example, the use of gold and/or platinum is possible for even only partial use on the resistors.

Two different electrical resistors therein can have different material strengths that are chosen such that they demonstrate varying resistance against corrosion.

A further embodiment of the invention envisions an aircraft having a corrosion detection apparatus according to one of the previous or subsequent embodiments.

According to a further embodiment of the invention, the corrosion-sensitive bridging element is selected from the group consisting of an electrically bridging element within the condenser, an electrically bridging element between conducting paths of the RFID resonant circuit, a corrosion-sensitive electrical resistor in the active resonant circuit, an electrical bridging of the inductivity of the resonant circuit, and any combination thereof.

Furthermore, it is possible for at least two of the parallel-connected corrosion-sensitive bridging elements to differ in terms of one parameter that is selected from the group consisting of electrical resistor, geometric dimension, thickness, material, additional corrosion-resistant coating layers and any combination thereof.

Regarding this and any other embodiment, it is to be noted that the bridging element need not necessarily be destroyed completely by corrosion in order to achieve the effect according to the invention, whereby a short does not necessarily have to be neutralized. Any change of the electrical conductivity can provide the user with the possibility of detecting the presence of corrosion on the component that is to be monitored.

According to a further embodiment of the invention using the RFID resonant circuit as described above, it is possible to send the identification information of the sensor circuit to a read-out device that allows for spatially localizing the identified component on the basis of the identification information.

Thus, it is possible to examine corroded components cheaply, quickly and with reduced measuring complexity. The invention is suitable for monitoring the ambient conditions of a component that is to be monitored by means of the invention.

BRIEF DESCRIPTION OF THE FIGURES

The representations below are schematic in nature and not drawn to scale.

Figure 1:
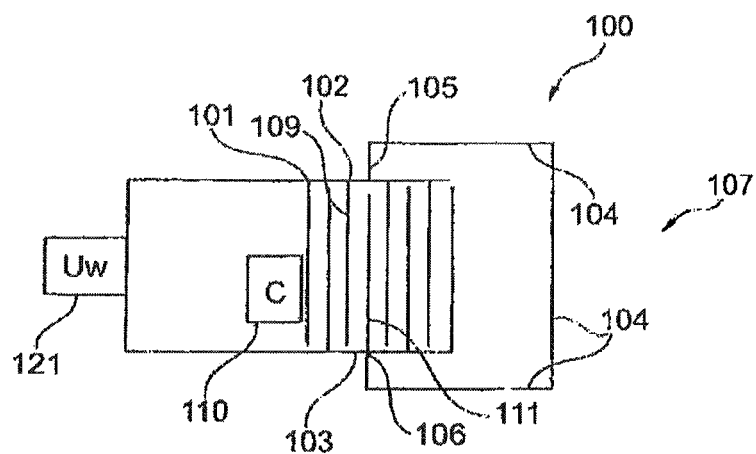
FIG. 1 is a schematic, two-dimensional representation of the corrosion detection apparatus according to an embodiment of the invention.

Referring to the figures, preferred embodiments of the present invention will be described below.

Identical or similar elements in the description of the figures shall be assigned identical reference numerals.

The information provided herein also applies to an aircraft that is equipped with a corrosion detection apparatus, which is an embodiment of the present invention.

DETAILED DESCRIPTION

FIG. 1 shows a corrosion detection apparatus 100 for permanently and integrally monitoring a state of corrosion of a component, wherein the corrosion detection device includes a sensor circuit 101 for detecting corrosion on the component. The sensor circuit includes a first electrical conducting section 102 and a second conducting section 103. In the present embodiment of the invention, a conducting section is configured as electrodes 109 and 111 of a condenser 110.

In this embodiment as depicted in FIG. 1, the condenser is depicted as an interdigital condenser having a plurality of interlocking fingers. Furthermore, the sensor circuit shows a bridging element 104 that is sensitive to corrosion having a first end 105 and a second end 106. Moreover, the first end with the first conducting section 102 and the second end with the second conducting section 103 are in an electrically conducting connection in the initial state 107, as presently shown. The initial state shows the situation in which corrosion has not yet caused an interruption of the electrically conducting connection through element 104.

It is also characteristic for the corrosion-sensitive bridging element according to the invention that the effects of any corrosion occurring on the bridging element, and thereby on the component that is to be monitored, are cumulative and add up over time, whereby an integral measurement of corrosion over time is possible.

Figure 2:
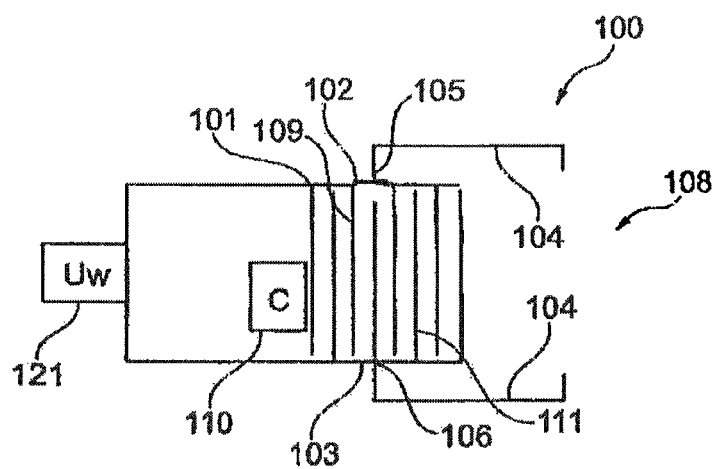
FIG. 2 is a schematic, two-dimensional representation of a corrosion detection device according to an embodiment of the invention.

In comparison to FIG. 2, which illustrates a state of corrosion 108, FIG. 1 thus shows a short-circuited interdigital condenser the capacitance of which cannot be determined using the applied voltage from the voltage source 121, due to the short circuit by the corrosion-sensitive bridging element.

FIG. 2, however, shows the determination of capacitance in the state of corrosion 108 below of the detection apparatus 100. Due to corrosion, the corrosion-sensitive bridging element has been interrupted in a region on the right edge of the image, thus allowing for electrostatic charging of the condenser 110 to occur. It is possible to determine the capacitance.

Figure 3:
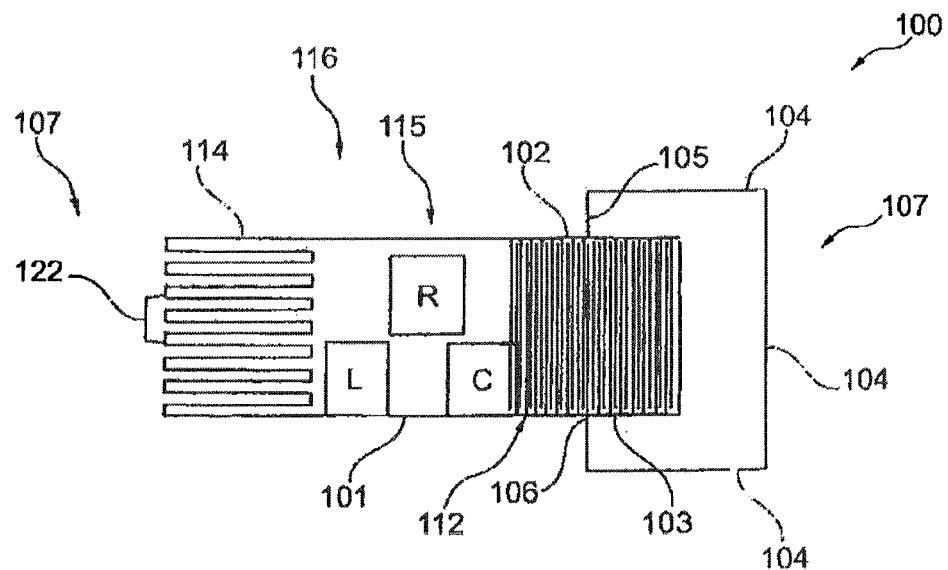
FIG. 3 is a schematic, two-dimensional representation of a corrosion detection apparatus according to an embodiment of the invention.
Figure 4:
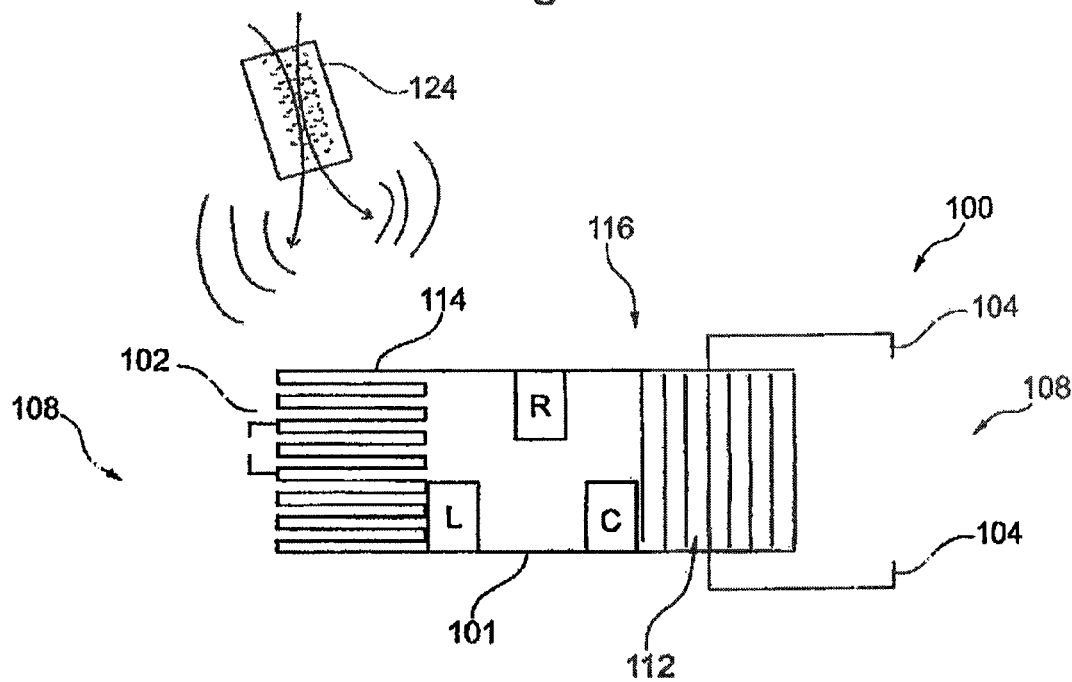
FIG. 4 is a schematic, two-dimensional representation of a corrosion detection apparatus according to an embodiment of the invention.

FIGS. 3 and 4 illustrate a detection apparatus 100, wherein in FIG. 3 the apparatus is in the initial state 107, in FIG. 4 in the state of corrosion 108. The corrosion detection apparatus therein includes a RFID resonant circuit 116. FIG. 3 shows a sensor circuit 101 in a first and a second conducting section 102 and 103. The interdigital condenser 112, which is part of the RFID resonant circuit, is in a shorted state in FIG. 3, because the corrosion-sensitive bridging element 104 creates the electrical short. This causes the RFID resonant circuit to be placed in an inactive state, whereby it cannot be read from the outside.

The coil 114 as shown on the left edge of the image of FIG. 3 can include, in addition to or in the alternative to the bridging of the condenser, a connecting wire 122 that creates the short between different windings of the coil 114.

Only after correspondingly accumulated environmental influences, such as, for example, moisture and temperature, is the corrosion able to neutralize the short circuit by means of the corrosion-sensitive bridging elements 104 and 122. This situation is shown in FIG. 4. Due to the neutralized shorts, it is possible to provide the resonant circuit, if necessary, with energy using a RFID read-out device 124, whereby excitation for sending a corresponding reply is created. In other words, in the event that an answer is detected by such an RFID resonant circuit, it is ensured that a corresponding corrosion on the sensor circuit, and thereby on the component that is to be monitored (not shown here), has indeed occurred. The corrosion-sensitive bridging element can be manufactured of a material that is, for example, the same material as the component that is to be examined. In case of an aircraft, it is possible for this material to be an aluminum alloy, for example.

However, it is also possible, while not shown in FIG. 3 or 4, for a RFID resonant circuit to maintain the resonant circuit in an active state by means of a plurality of conducting path resistances such as, for example, ohmic resistors, while changing the resonant frequency and attenuation of the same by means of said resistors. Consequent to advancing corrosion, the resistance continually increases, which becomes noticeable, in turn, in a change of the resonant frequency and attenuation. In other words, based on a measurement of a change of these two values, it is possible to detect a state of corrosion of the component.

Figure 5:
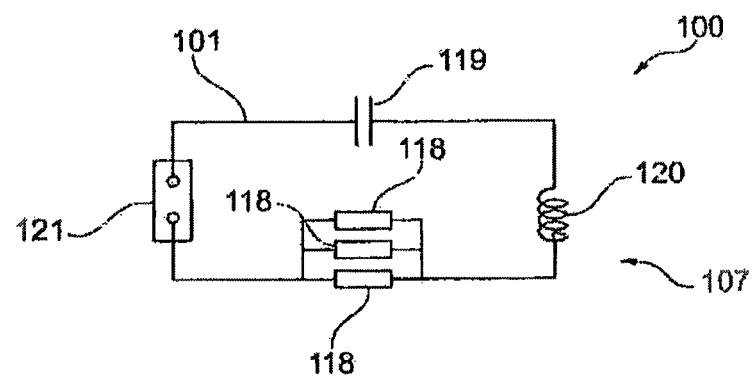
FIG. 5 is a schematic, two-dimensional representation of a corrosion detection apparatus according to an embodiment of the invention.

FIG. 5 shows a corrosion detection apparatus 100 having a sensor circuit 101 that includes a condenser 119 and a coil 120. This embodiment illustrates the initial state 107 that provides for three parallel-connected corrosion-sensitive bridging elements 118, as shown. These three parallel resistors can have, for example, varying material strengths. Corrosion therein will first deactivate the resistors having a small material strength. A remaining resistor that is either protected against corrosion, such as, for example, by a coating, or that is made of a material that is resistant to corrosion, such as, for example, gold or platinum or an alloy thereof, ultimately preserves the functionality of the resonant circuit. For this resonant circuit as shown in FIG. 5, further components of a RFID resonant circuit can be present, such as, for example, a storage means or an antenna. However, these elements are not shown FIG. 5.

Figure 6:
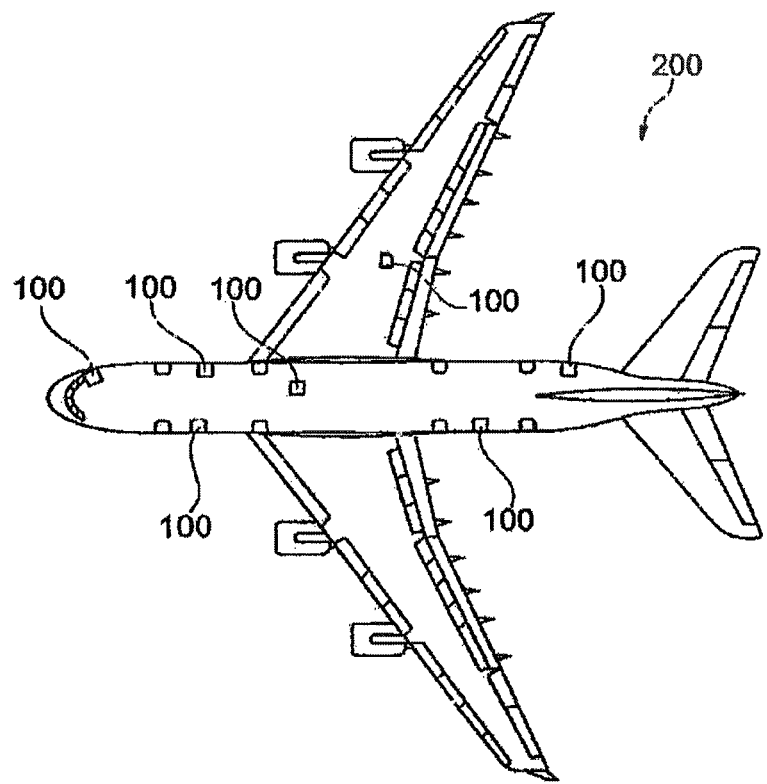
FIG. 6 shows an aircraft with a corrosion detection apparatus according to an embodiment of the present invention.

FIG. 6 shows an aircraft 200 that is configured as an airplane in the present embodiment, wherein the airplane includes a plurality of corrosion detection apparatuses at various locations. It is possible therein for the corrosion detection apparatus to be used preferably on the interior of the airplane, for example, inside the cabin or cargo space.

In addition, it is to be noted that the terms "comprising" and "including" do not exclude other elements or steps and that the singular article "a" or "an" does not exclude a plurality. Furthermore, the characteristics or steps that have been described in reference to the embodiments as outlined above can also be used in combination with other characteristics or steps or others of the above-described embodiments. A limiting effect is explicitly excluded to apply regarding the reference symbols as set forth in the claims.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

The invention claimed is:

1. A corrosion detection apparatus for permanently and integrally monitoring a state of corrosion of a component, wherein the corrosion detection apparatus comprises:
   a sensor circuit configured to detect corrosion on the component, wherein the sensor circuit includes
   a first electrical line section;
   a second electrical line section; and
   a corrosion-sensitive bridging element having a first end and a second end,
   wherein, in a initial state, the first end is in electrical connection with the first line section and the second end is in contact with the second line section,
   wherein the corrosions-sensitive bridging element has a first electrical conductivity in the initial state and a second electrical conductivity in a corrosion state such that the sensor circuit detects corrosion on the basis of the change from the first to the second electrical conductivity,
   wherein the first electrical line section is a first electrode of a condenser and the second electrical line section is a second electrode of the condenser,
   wherein the condenser is an interdigital condenser and the corrosion-sensitive bridging element is a thin layer between two electrodes of the interdigital condenser.

2. The corrosion detection apparatus according to claim 1, wherein the condenser is short-circuited in the initial state.

3. The corrosion detection apparatus according to claim 2, wherein the sensor circuit is an RFID resonant circuit.

4. The corrosion detection apparatus according to claim 3, wherein the RFID resonant circuit comprises:
   an antenna configured to send and receive electromagnetic signals and an analog circuit with an electrical capacitance and an electrical inductivity,
   wherein the corrosion-sensitive bridging element is configured to electrically bridge the RFID resonant circuit in the initial state.

5. The corrosion detection apparatus according to claim 4, wherein the sensor circuit is configured such that a read-out is possible selected from the group consisting of reverse phase reflecting of a field that is created by a read-out device, weaknesses of a field created by the read-out device, read-out by means of load modulation, and any combination thereof.

6. The corrosion detection apparatus according to claim 2, wherein the sensor circuit includes a plurality of parallel-connected corrosion-sensitive bridging elements, which are dimensioned in relation to each other such that they correspond to a preset characteristic of corrosion over time.

7. The corrosion detection apparatus according to claim 2, wherein the corrosion detection apparatus further comprises:
   a read-out device configured to measure electrical properties of an apparatus comprising the first line section, the second line section and the corrosion-sensitive bridging element.

8. An aircraft, comprising:
   a corrosion detection apparatus configured to permanently and integrally monitor a state of corrosion of a component, wherein the corrosion detection apparatus comprises
   a sensor circuit configured to detect corrosion on the component, wherein the sensor circuit includes
      a first electrical line section;
      a second electrical line section; and
      a corrosion-sensitive bridging element having a first end and a second end,
   wherein, in a initial state, the first end is in electrical connection with the first line section and the second end is in contact with the second line section,
   wherein the corrosions-sensitive bridging element has a first electrical conductivity in the initial state and a second electrical conductivity in a corrosion state such that the sensor circuit detects corrosion on the basis of the change from the first to the second electrical conductivity,
   wherein the first electrical line section is a first electrode of a condenser and the second electrical line section is a second electrode of the condenser,
   wherein the condenser is an interdigital condenser and the corrosion-sensitive bridging element is a thin layer between two electrodes of the interdigital condenser.

9. The aircraft according to claim 8, wherein the condenser is short-circuited in the initial state.

10. The aircraft according to claim 9, wherein the corrosion detection apparatus further comprises:
   a read-out device configured to measure electrical properties of an apparatus comprising the first line section, the second line section and the corrosion-sensitive bridging element.

11. The aircraft according to claim 9, wherein the sensor circuit is an RFID resonant circuit.

12. The aircraft according to claim 11, wherein the RFID resonant circuit comprises:
   an antenna configured to send and receive electromagnetic signals and an analog circuit with an electrical capacitance and an electrical inductivity,
   wherein the corrosion-sensitive bridging element is configured to electrically bridge the RFID resonant circuit in the initial state.

13. The aircraft according to claim 12, wherein the sensor circuit is configured such that a read-out is possible selected from the group consisting of reverse phase reflecting of a field that is created by a read-out device, weaknesses of a field created by the read-out device, read-out by means of load modulation, and any combination thereof.

14. The aircraft according to claim 9, wherein the sensor circuit includes a plurality of parallel-connected corrosion-sensitive bridging elements, which are dimensioned in relation to each other such that they correspond to a preset characteristic of corrosion over time.

\* \* \* \* \*